(12) United States Patent
Levisman

(10) Patent No.: US 6,702,739 B2
(45) Date of Patent: Mar. 9, 2004

(54) HOLDER

(75) Inventor: Ricardo Levisman, Aguero 1292 - 1° piso, 1425 Ciudad de Buenos Aires (AR)

(73) Assignee: Ricardo Levisman, Buenos Aires (AR)

(*) Notice: Subject to any disclaimer, the term of this patent is extended or adjusted under 35 U.S.C. 154(b) by 156 days.

(21) Appl. No.: 10/036,134

(22) Filed: Nov. 9, 2001

(65) Prior Publication Data

US 2002/0087051 A1 Jul. 4, 2002

Related U.S. Application Data

(63) Continuation of application No. 09/650,542, filed on Aug. 30, 2000, now abandoned.

(51) Int. Cl.$^7$ ................................................. A61B 1/32
(52) U.S. Cl. ........................................ 600/217; 600/237
(58) Field of Search ............................ 600/201, 206, 600/209, 217, 218, 219, 235, 237, 238, 243, 244; 606/221; 269/53, 54.5; 81/485; 433/136, 140

(56) References Cited

U.S. PATENT DOCUMENTS

| 1,123,290 A | 1/1915 | Von Herff ..................... 606/221 |
| 1,389,436 A | 8/1921 | Cameron ..................... 600/217 |
| 1,450,419 A | 4/1923 | Heidbrink ..................... 600/237 |
| 2,238,563 A | 4/1941 | Jacques |
| 2,581,679 A | * 1/1952 | Marshall |
| 5,921,979 A | 7/1999 | Kovac et al. ..................... 606/1 |

FOREIGN PATENT DOCUMENTS

DE 467698 10/1928

* cited by examiner

Primary Examiner—Cary E. O'Connor
(74) Attorney, Agent, or Firm—Greer, Burns & Crain, Ltd.

(57) ABSTRACT

A holder for holding parts of a body, structure or assembly spaced apart during operations carried out on the body, structure or assembly, the retractor comprising a body made of wire and having a resilient hinge portion at a vertex of the body and at least two arms outwardly extending from the hinge portion, each arm having a distal portion including anchoring tips.

26 Claims, 3 Drawing Sheets

HOLDER

This application is a continuation in part of U.S. Ser. No. 09/650,542, filed Aug. 30, 2000, now abandoned.

BACKGROUND OF THE INVENTION

1. Field of the Invention

The present invention relates to a holder and/or retractor, particularly a retractor for use in the medical field for holding or keeping parts of a patient's body separated to facilitate a treatment of the body, and more particularly, the retractor is for retracting flaps in surgery and, even more particularly, for surgery in odontology or oral implantology.

While specific references will be made in the present application to oral surgery and implantology, it must be clear that the retractor of the invention may be widely applied to a number of activities such as general surgery in the medical field, general manual works in several fields like carpentry, hobbies, etc. When the term retractor is used in this application reference is made to the use of the inventive holder to bring the involved parts to a separate fashion and when the term holder is used it means that the holder may be used for retracting parts or keeping parts closed together under a pressure from the resiliency of the holder.

2. Description of the Prior Art

It is well known in any surgical operation that some parts of the patient's body must be kept separated to have sufficient access to the areas under operation. It is well know to provide holders, retractors or separators, as they are well known in the art, to guarantee that the flaps at both sides of the incision remain separated and spaced apart from each other to permit an adequate exposure of the internal organs, bone, etc.

In oral implantology, for instance, incisions must be made on the crest of the ridge. Then, a flap reflection is made with a sharp periosteal elevator to expose enough bone area for the osteotomy and retraction of the flaps must also be made to start with the perforations in the bone for receiving the implants. The flap retraction is carried out by retractor devices which must be manually held by an assistant during operations carried out by the implantologist. Due to the very small room available at the mouth of the patient, the several works involved in the operation until obtaining a proper positioning of the implant become very uncomfortable not only for the implantologist and the assistant but also to the patient.

The above mentioned retractors of the prior art generally comprise large devices with handles that must be retained by the hand of the odontologist and/or the assistant outside the mouth of the patient. One type of retractor comprises a fork-like device having an elongated handle with a shank terminating in one or more prongs used for holding the flaps spaced apart at both sides of an incision. The operation is performed with the implantologist at one side of the patient, handling all the surgery instruments, and the assistant at the opposite side of the patient holding not only the retractors but also handling several other implements like the saliva and blood suckers. When a surgical operation is extended for a long time, the assistant feels his/her arms very tired and becomes tired and unable to hold the retractors in a proper fashion which causes the implantologist to interrupt the operations, with the risk for the patient and the further extension of time in the operation.

Another type of separator or retractor comprises a scissors-like device comprising two retracting arms connected to respective handles that are movable one towards the other and connected to each other at a central pivot connection in a manner that when the handles are moved in a closing fashion the arms move outwardly in an opening fashion, that is one far away from the other. To hold flaps separated the arms are provided at distal ends thereof with one or more prongs. With the arms closed, that is one engaged to the other, the prongs are inserted in the incision between the flaps and the handles are moved in a closing fashion to cause the arms to open. Locking means are provided in the handles to lock the device with the arms in the open position to hold the flaps separated and spaced apart from each other. It is well apparent to any person skilled in the art that all these operations and maneuvers carried out by two persons in the mouth of a patient is not an easy task but a complex and cumbersome handling.

U.S. Pat. No. 1,450,419 to Heidbrink discloses a dental device for spreading tissues, the device comprising two arms of a wire coiled at its middle to form a spring portion at the rear of the device so that the two arms are resiliently urged outwardly in opposite directions, with the ends of the arms terminating in respective sharpened points to be inserted into the tissue at opposite sides of an incision. As it is better shown in FIG. 2 of the patent, the device is bulky and difficult to be accommodated into the patient's mouth, particularly when the incision must be made between two dental pieces that are closed to each other without enough room existing to make the incision and place the retractor. In addition, the sharpened points tend to pass entirely through the tissue and even cut the tissue as long as there is no means, such as a back plate, to prevent the pins from excessively entering and passing through the tissue.

U.S. Pat. No. 2,238,563 to Jacques discloses an embalming instrument comprising a pair of metallic bowed arms normally tending to spring apart and away from each other at the free ends, with a coil portion formed in substantially the same plane as the arms. The free ends of the arms include plates secured thereto forming incision engaging means and including piercing members sharpened at their outer ends and forming needle points for piercing the tissue and keeping it open over the incision. While the plates tend to prevent the needle points from excessively running through the tissue, thus preventing the tearing of same. The provision of only one needle point at each side of the incision does not prevent the pivoting of the retractor around the piercing points with the subsequent uprising movement of the retractor forming an obstacle on the incision area.

It would be therefore convenient to have a retractor that may be easily handled to place it between the flaps of an incision with a hand only and that is capable of holding the flaps spaced apart from each other in a stable condition without the help of any assistant, and with the retractor firmly retained in the tissue without moving or uprising after the placing thereof in the incision.

SUMMARY OF THE INVENTION

It is therefore one object of the present invention to provide a retractor for holding parts, portions or components of a body, structure or assembly, spaced apart during operations carried out on the body, structure or assembly, the retractor comprising a body having a resilient hinge portion at a vertex of the body and at least two arms outwardly extending from the hinge portion, each arm having a distal portion including anchoring means.

It is still another object of the present invention to provide a retractor or holder for holding body parts of a patient separated from each other or engaged together during treating operations carried out on the patient for medical purposes, the retractor comprising at least a body made of wire and having a resilient hinge portion and at least two arms outwardly extending from the hinge portion, each arm comprising: a distal arm portion, a proximal arm portion having at least a portion thereof extending angularly to the distal arm portion, first anchoring means provided at a distal end of the distal arm portion, and second anchoring means provided in the distal arm portion between the first anchoring means and a joint between the distal arm portion and the proximal arm portion.

It is still another object of the present invention to provide a holder or retractor for holding parts of an assembly separated from each other or close to each other during working operations carried out on the assembly, the holder comprising at least a wire body having a resilient hinge portion and at least two arms outwardly extending from the hinge portion, each arm comprising a distal arm portion, a proximal arm portion having at least a portion thereof extending angularly to the distal arm portion, first anchoring means provided at a distal end of the distal arm portion, and second anchoring means provided in the distal arm portion between the first anchoring means and a joint between the distal arm portion and the proximal arm portion.

It is a further object of the present invention to provide the abovementioned holder wherein the at least one portion of the proximal arm portion extending angularly to the distal arm portion defines an intermediate arm portion and the second anchoring means are placed between the first anchoring means and a joint between the intermediate arm portion and the distal arm portion.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

DESCRIPTION OF THE PREFERRED EMBODIMENTS

Figure 1:
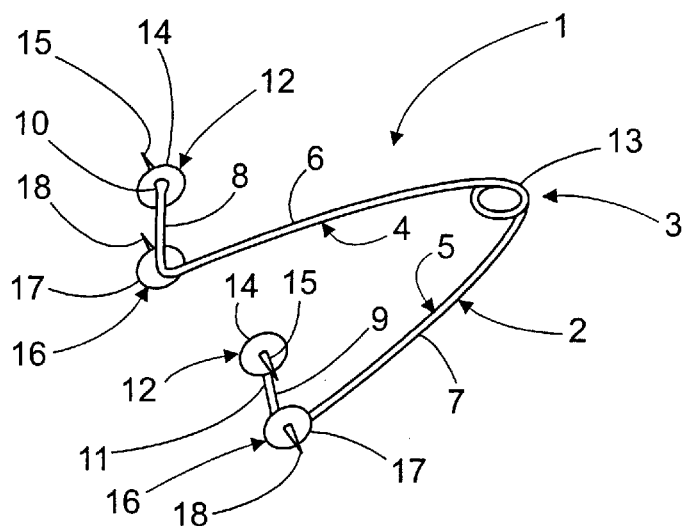
FIG. 1 shows a perspective, top view of a retractor according to a first embodiment of the invention.

Now referring in detail to the drawings it may be seen from FIG. 1 a first embodiment of the invention wherein the retractor 1 is preferably used for holding parts of a patient separated from each other during treating operations carried out on the patient for medical purposes. Retractor 1 comprises an integral body 2 made of wire, preferably of stainless steel or any other bio compatible material, most preferably a resilient material, with resilient memory. Body 2 comprises a resilient hinge portion 3 and at least two arms 4, 5 outwardly extending from the hinge portion, each arm 4, 5, comprising a proximal arm portion 6, 7, and a distal arm portion 8, 9. Proximal arm portion 6, 7, extends angularly, and preferably normally, relative to distal arm portion 8, 9. While the entire proximal arm portion 6, 7 extends angularly or normally to the distal arm portion 8, 9, the proximal arm portion may have only a part thereof or at least a portion thereof extending angularly or normally to the distal portion with the remaining part of the proximal arm portion extending parallel, for example, to the distal arm portion, as it will be disclosed in connection to FIG. 2. Each distal arm portion 8, 9, includes a distal end 10, 11 including respective first anchoring means 12.

Figure 2:
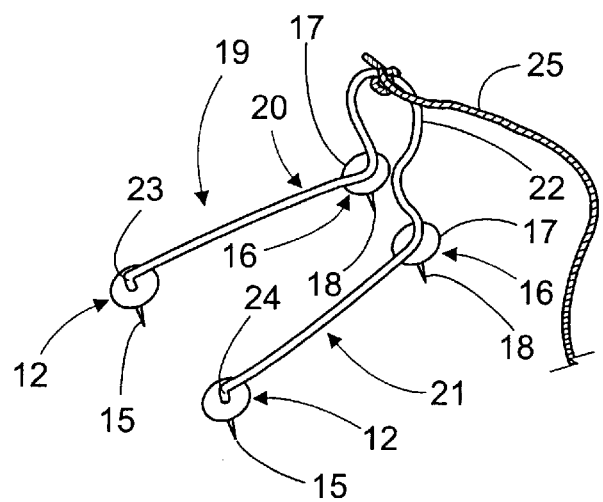
FIG. 2 shows a perspective, top view of a retractor according to another embodiment of the invention.

Body 2 is integrally made of wire, therefore the hinge portion and the arms being integral. The hinge portion is defined by a coil 13 or spiral made by wire wound around an axis. Hinge means may also be defined by a loop in the wire extending as it is shown in FIG. 2 in relation to another embodiment to which reference will be made later. Each anchoring means 12 preferably comprises a back plate 14 and a sharp tip 15 normally extended from the back plate. Sharp tip 15 is configured to pinch the flaps of tissue or gum of the patient and back plate 14 is able to define a back support or stop by engaging the flap thus improving the holding thereof. Any angle may be defined between pin or tip and back support 14 provided that the tip can always be retained in the tissue.

Second anchoring means 16 are provided in the distal arm portion between first anchoring means 12 and a joint between the distal arm portion and the proximal arm portion. Second anchoring means are like the first anchoring means and each second anchoring means 16 comprises a support or back plate 17 and a sharp tip 18 normally extending from plate 17. While tips 15 and 18 are illustrated as extending normally, the same may be placed forming any convenient angle relative to the corresponding plate 14, 17. The size of plate 14, 17 is enough to not bar the operation works of the surgeon but large enough to prevent the tip from running entirely through the tissue or flaps and tearing the tissue.

FIG. 2 shows another alternative retractor according to the invention wherein the retractor, indicated by general reference number 19, comprises a wire made body with a resilient hinge portion defined by a loop 22 formed in the wire and extending normally to distal arm portions 20, 21 which in turn extend outwardly from the hinge portion, each arm portion 20, 21 having a respective distal end 23, 24, each end including respective anchoring means 12. According to this embodiment, loop 22 directly forms a proximal arm portion, in other words, the proximal arm portion is formed in such a manner to form a resilient hinge. In addition to any resiliency that arms may have, the proximal arm portion and, more particularly loop 22, provides the arms with enough resiliency to recover any initial position after being opened or closed under an external pressure. In this embodiment first and second anchoring means 12 and 16, more particularly tips 15 and 18, extend downwardly and are parallel to each other giving another possibility of application of the inventive retractor. Thread 25 may also be provided in this embodiment as well as in the remaining embodiments of the invention.

Figure 3:
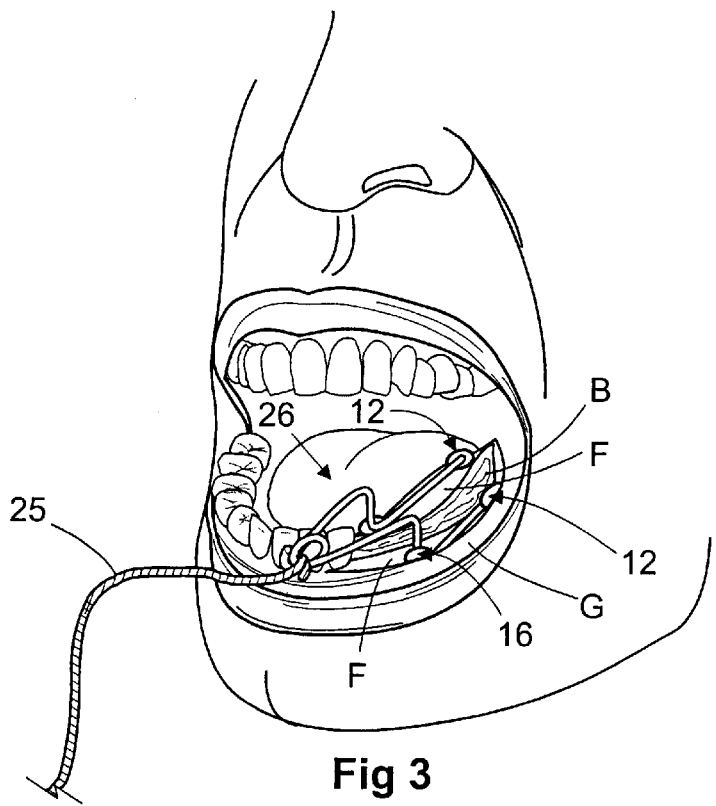
FIG. 3 shows a perspective view of the retractor of FIG. 4 as applied into the mouth of a patient to hold flaps spaced apart during a surgical operation.
Figure 4:
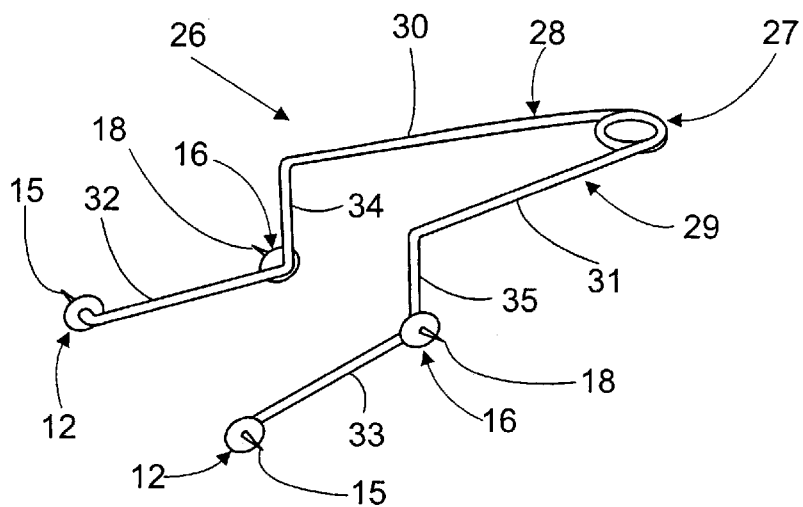
FIG. 4 shows a perspective, top view of a retractor according to another embodiment of the invention.

FIG. 4 shows another alternative retractor according to the invention wherein retractor 26 comprises a hinge portion 27 formed by a coil or spiral 27 and arms 28, 29 extending from the coil and respectively formed by a distal arm portion 32, 33 and a proximal arm portion 30, 31 having at least a portion thereof that forms an angle with the corresponding distal arm portion and defines an intermediate arm portion 34, 35. Distal arm portions 32, 33 are respectively connected to the proximal arm portions by intermediate arm portions 34, 35 extending normally to the proximal and distal arm portions. The first anchoring means, also indicated by reference 12 are provided at a distal end of the distal arm portions and the second anchoring means 16 are provided at a joint between the distal arm portions and the intermediate arm portions. The holder of FIG. 4 may be appropriate for use when 3 or 4 dental pieces are lacking in the area under operation with longer flaps resulting from the incision and longer arms with more anchoring means are necessary. An application of this embodiment is illustrated in FIG. 3.

During a surgical operation, in classical oral implantology, for instance, an incision is made on gum G to have a sufficient exposure of the bony crest B wherein the bores for receiving the implants are to be drilled. In order to keep flaps F spaced apart enough to have free access to bone B retractor 26 of the invention is positioned within, or partially within the mouth of the patient, preferably in the position shown in FIG. 3, with anchoring means 12 and 16 inserted between the flaps in order that tips 15 and 18 (not shown) are piercing the flaps and back plates rest against an inner side of the flaps. Before introduction within the incision, retractor 26 is closed by exerting pressure over its arms 30, 31 in order to bring them to be closer, that is, in a closing fashion. Once the arms are close together, tips are introduced at the bottom of the flaps and pierced against the flaps and the retractor is left free in order to self expand outwardly under its resilient memory thus bringing the flaps far away from each other and expose the bone for any operation to be carried out on same. While FIG. 3 shows the anchoring means piercing the flaps close to an upper edge thereof for illustrative purposes it is recommended to pierce tips 15 and 18 at the bottom part of the flaps. The retractor will remain open without the need of any external assistance from the implantologist or his/her assistant. To prevent the retractor from becoming disengaged from the flaps with the risk of being swallowed by the patient, the retractor is preferably provided with a cord or thread 25 with an end of the thread tied at any portion of the retractor and an opposite end of the thread tied at any part outside the mouth of the patient, at the patient's clothes, for example.

Figure 5:
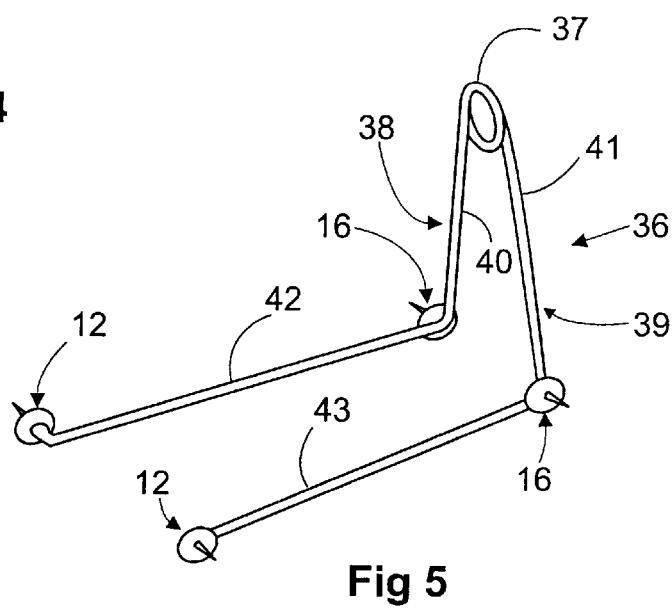
FIG. 5 shows a perspective, top view of a retractor according to another embodiment of the invention.

FIG. 5 shows a retractor indicated by reference number 36 similar to the holder of FIG. 1, with hinge portion formed by a coil or spiral 37 and arms 38, 39 extending from the coil and respectively formed by a proximal arm portion 40, 41 and a distal arm portion 42, 43 extending normally to the respective proximal arm portions 40, 41. The first anchoring means, also indicated by reference 12 are provided at a distal end of the distal arm portions 42, 43 and the second anchoring means, indicated also by reference 16, are provided at a joint between distal arm portions 42, 43 and proximal arm portions 40, 41. The holder of FIGS. 1–5 may be appropriate for use when dental pieces are lacking in the area under operation, with the arms and anchoring means sufficient to hold the flaps between the teeth.

Figure 6:
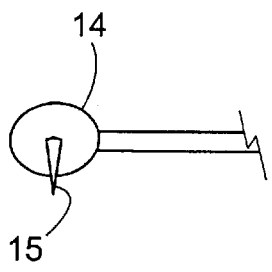
FIGS. 6–8 show several perspective views of anchoring means applied at distal ends of the arms of the retractor of the invention.
Figure 7:
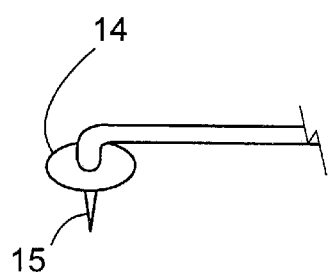
Figure 8:
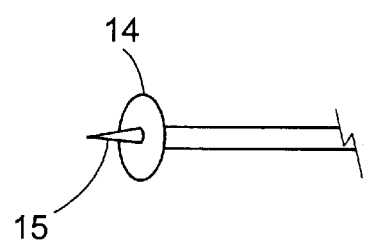

FIGS. 6 to 8 show different configurations for first anchoring means wherein the back plate 14 and the sharp tips 15 are oriented in several directions according to the preferred application thereof. Since the anchoring means in the three embodiments are equivalent the same reference numbers like in the remaining Figures have been used for indicating the plate and tip. While only the first anchoring means have been illustrated in the corresponding distal ends of the corresponding arms, the capability of been oriented in the positions illustrated in FIGS. 6–8 is also applied for second anchoring means 16.

Figure 9:
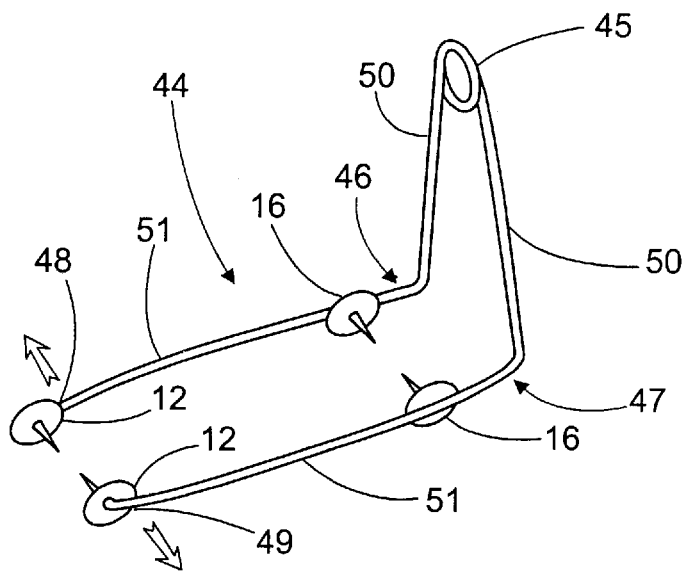
FIG. 9 shows a perspective, top view of a retractor according to another embodiment of the invention, used for applying pressure between parts of a body for helping in suturing an incision, for example.

FIG. 9 shows another alternative holder of the invention, this holder, indicated by reference number 44, comprises an integral body also made of wire, preferably of stainless steel or any other bio compatible material, most preferably a resilient material, with resilient memory that brings the holder to be in a close mode as it is illustrated in FIG. 9. The holder 44 comprises a resilient hinge portion 45 and at least two arms 46, 47 outwardly extending from the hinge portion, each arm 46, 47 having respective distal ends 48, 49 as well as proximal 50 and distal 51 arm portions normally arranged to each other, and each distal end includes anchoring means 12. Second anchoring means 16 are provided between the first anchoring means and close or at the joint between the proximal and distal arm portions, but second anchoring means could also be provided at the corresponding joint. The hinge portion is defined by a coil or spiral. First and second anchoring means 12 and 16, respectively, each also comprises a back plate 14 and a sharp tip 15 normally extended from the back plate. According to this embodiment, first and second anchoring means 12 and 16 are configured in a facing pattern or fashion, one extending towards the other, to pinch the flaps of tissue or gum of the patient. In like manner, back plate 14 is able to define a back support or stop by engaging the flap thus improving the holding thereof.

After the surgical operation, as illustrated and described in relation to FIG. 3, has ended, the flaps must be brought to close the incision and engage, as much as possible, one to the other. At this stage of the operation, holder 44 is opened, for example manually, and each sharp tip is pinched against each flap F in order to keep the flaps engaged together to permit the surgeon to make the suture easily without the need of any assistant to retain the flaps in a proper position for suturing.

Figure 10:
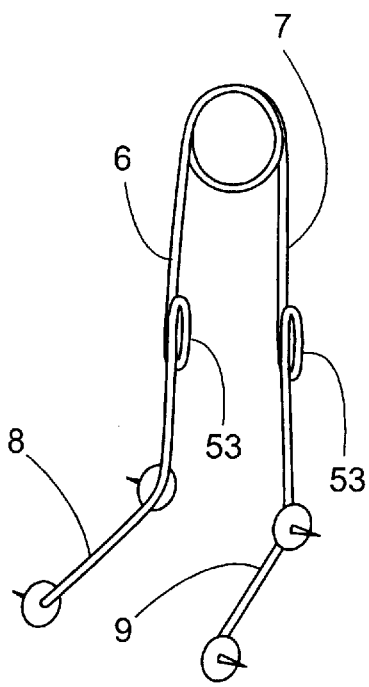
FIGS. 10 and 11 show perspective, top views of retractors according to other embodiments of the invention, incorporating handling means for enhancing the gripping of the holder by the odontologist's fingers.
Figure 11:
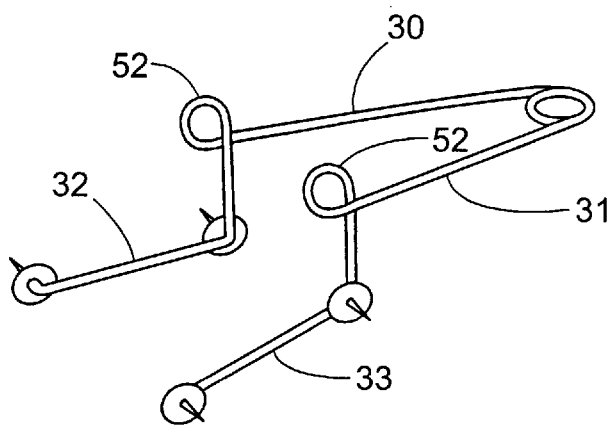

Further alternatives are illustrated in FIGS. 10 and 11 wherein an inventive holder or retractor, similar to those shown in FIGS. 1 and 4, respectively, both holders incorporating handling means 52 and 53 for permitting the user, namely the odontologist, implantologist, etc., to firmly grip the holder by means of only two fingers without the holder to slip off the fingers when it is under pressure. The remaining structures of the holders of FIGS. 10 and 11 are the same as the ones of FIGS. 1 and 4, therefore no additional description is made thereof. The handling means 52, 53 may consist basically of a loop made in the wire, preferably at a joint between the proximal arm portion 30, 31 and the intermediate arm portion 34, 35, in holder 26, or in any convenient place of proximal arm portion 40, 41 in holder 36. The handling means 52, 53 may be, however, provided in any of the other embodiments and not only in the proximal arm portion but also, or alternatively, in the distal arm portion. For example, handle means 52, 53 may be provided in arm portions 20, 21 of the alternative holder shown in FIG. 2. In other words, the handling means for gripping the holder with a user's fingers are provided in at least one of the proximal and distal arm portions in any of the inventive embodiments.

The wire used for the inventive holder is preferably a wire having a diameter of 1–2 mm, with a circular cross-section. In any event any other cross-section may be used as long as the body is not bulky and conserves the necessary resiliency and memory. Because of its size and wire nature, the inventive holder provides a clear space for working in the patient's mouth and it does not obstruct the implantologist's view.

Because of the particular disclosed and illustrated arrangement of the first and second anchoring means along the distal arm portions, the inventive holder will be firmly retained in the flaps without any possibility of rotation or movement during the operation.

In all of the above disclosed embodiments the retractor preferably comprises an integral body made of wire, preferably of stainless steel or any other bio compatible material, a plastics for example, most preferably a resilient material, with resilient memory. Therefore the hinge portion and the arms form an integral body. In addition to the natural resiliency of the arms, the hinge portion provides the arms with the capacity of recovering their initial position either after a closing or opening pressure exerted by an external force. While back plate 14 has been illustrated as being circular in all of the embodiments, it is clear for any person skilled in the art that the plate may have any configuration such as square, rectangular, polygonal, etc. The stainless steel is preferably employed because it is resistant to the new sterilization systems such as the autoclave, using a wet environment, or in ultrasound techniques using corrosive fluids.

Depending on the room available into the mouth of the patient as well as of the teeth conditions any of the above-described retractors according to the invention may be properly used according to the implantologist needs and criteria. In like manner any of the described holders may be used alone or in combination. Also, while each of the several holders has been shown in a particular position, this position is for illustrative purposes only and the holder will be used and positioned in the patient's mouth in the proper position and orientation depending on which part of the gum is made the incision and whether the upper or the lower gum is under operation.

In addition to the foregoing, the relative lengths of the proximal and distal arm portions may be variable in such a manner that with only one holder design, for example that one of FIG. 4, the implantologist has a series of holders with different distal, or proximal, arm portion lengths for particular and several applications.

While preferred embodiments of the present invention have been illustrated and described, it will be obvious to those skilled in the art that various changes and modifications may be made therein without departing from the scope of the invention as defined in the appended claims.

I claim:

1. A holder for holding body parts of a patient separated from each other or engaged together during treating operations carried out on the patient for medical purposes, the holder comprising at least a body made of wire and having a resilient hinge portion and at least two arms outwardly extending from the hinge portion, each arm comprising:
    a distal arm portion,
    a proximal arm portion having at least a portion thereof extending angularly to the distal arm portion,
    first anchoring means provided at a distal end of the distal arm portion, and
    second anchoring means provided in the distal arm portion between the first anchoring means and at least one of at or near a joint between the distal arm portion and the proximal arm portion.

2. The holder of claim 1, wherein the wire body is integrally made of wire with the hinge portion and the arms being integral.

3. The holder of claim 2, wherein the at least one portion of the proximal arm portion extending angularly to the distal arm portion defines an intermediate arm portion and the second anchoring means are placed between the first anchoring means and a joint between the intermediate arm portion and the distal arm portion.

4. The holder of claim 3, wherein said intermediate arm portion extends normally to the proximal and distal arm portions.

5. The holder of claim 3, wherein the second anchoring means are placed at the joint between the intermediate arm portion and the distal arm portion.

6. The holder of claim 3, wherein the hinge portion is defined by a loop in the wire, the loop extending in a same plane as the proximal arm portion.

7. The holder of claim 3, wherein the anchoring means comprises a back plate and a sharp tip normally extended from the back plate.

8. The holder of claim 1, wherein said at least a portion of the proximal arm portion extends normally to the distal arm portion.

9. The holder of claim 1, wherein the hinge portion is defined by a loop in the wire, the loop extending angularly relative to the distal arm portion.

10. The holder of claim 4, wherein the loop extends normally to the distal arm portion.

11. The holder of claim 1, wherein the resilient hinge portion is defined by a coil.

12. The holder of claim 1, wherein the anchoring means comprises a back plate and a sharp tip.

13. The holder of claim 12, wherein the sharp tip is normally extended from a back plate.

14. The holder of claim 1, wherein the anchoring means comprises a back plate and a sharp tip normally extended from the back plate.

15. The holder of claim 1, wherein the entire proximal arm portion extends normally to the distal arm portion.

16. The holder of claim 1, wherein the wire body is made of resilient wire.

17. The holder of claim 1, wherein the wire is a stainless steel wire.

18. The holder of claim 1, wherein a thread is provided with an end of the thread tied to the holder and an opposite end to be tied at any other part to take control on the holder.

19. The holder of claim 1, wherein handling means for gripping the holder with a user's fingers are provided in at least one of the proximal and distal arm portions.

20. The holder of claim 19, wherein each handling means comprises a loop in the wire.

21. A holder for holding parts of an assembly separated from each other or close to each other during working operations carried out on the assembly, the holder comprising at least a wire body having a resilient hinge portion and at least two arms outwardly extending from the hinge portion, each arm comprising:
   a distal arm portion,
   a proximal arm portion having at least a portion thereof extending angularly to the distal arm portion,
   first anchoring means provided at a distal end of the distal arm portion, and
   second anchoring means provided in the distal arm portion between the first anchoring means and a joint between the distal arm portion and the proximal arm portion.

22. The holder of claim 21, wherein the at least one portion of the proximal arm portion extending angularly to the distal arm portion defines an intermediate arm portion and the second anchoring means are placed between the first anchoring means and a joint between the intermediate arm portion and the distal arm portion.

23. The holder of claim 22, wherein the anchoring means comprises a back plate and a sharp tip normally extended from the back plate.

24. The holder of claim 23, wherein the back plate has a configuration selected from circular, square, rectangular and polygonal.

25. The holder of claim 21, wherein handling means for gripping the holder with a user's fingers are provided in at least one of the proximal and distal arm portions.

26. The holder of claim 25, wherein each handling means comprises a loop in the wire.

* * * * *